United States Patent
Penninger et al.

(10) Patent No.: US 12,303,689 B2
(45) Date of Patent: May 20, 2025

(54) POLYPHONIC PITCH ENHANCEMENT IN A COCHLEAR IMPLANT

(71) Applicant: MED-EL Elektromedizinische Geraete GmbH, Innsbruck (AT)

(72) Inventors: Richard Penninger, Innsbruck (AT); Dirk Meister, Innsbruck (AT)

(73) Assignee: MED-EL Elektromedizinische Geraete GmbH, Innsbruck (AT)

( * ) Notice: Subject to any disclaimer, the term of this patent is extended or adjusted under 35 U.S.C. 154(b) by 508 days.

(21) Appl. No.: 17/639,196

(22) PCT Filed: Aug. 28, 2020

(86) PCT No.: PCT/US2020/048386
§ 371 (c)(1),
(2) Date: Feb. 28, 2022

(87) PCT Pub. No.: WO2021/041796
PCT Pub. Date: Mar. 4, 2021

(65) Prior Publication Data
US 2022/0323756 A1    Oct. 13, 2022

Related U.S. Application Data

(60) Provisional application No. 62/894,326, filed on Aug. 30, 2019.

(51) Int. Cl.
*A61N 1/36* (2006.01)
*A61N 1/02* (2006.01)
(Continued)

(52) U.S. Cl.
CPC ......... *A61N 1/36038* (2017.08); *A61N 1/025* (2013.01); *A61N 1/0541* (2013.01);
(Continued)

(58) Field of Classification Search
CPC .. A61N 1/025; A61N 1/0541; A61N 1/36038; A61N 1/36192; G10L 25/90;
(Continued)

(56) References Cited

U.S. PATENT DOCUMENTS

| | | |
|---|---|---|
| 4,357,497 A | 11/1982 | Hochmair et al. |
| 8,185,383 B2 | 5/2012 | Zeng et al. |

(Continued)

FOREIGN PATENT DOCUMENTS

WO    WO 2014/164814 A1    10/2014

OTHER PUBLICATIONS

International Searching Authority/EP, International Search Report and Written Opinion of the International Searching Authority, Application No. PCT/US2020/048386, mailed Nov. 6, 2020, 14 pages.

*Primary Examiner* — Amanda K Hulbert
(74) *Attorney, Agent, or Firm* — Barclay Damon LLP

(57) ABSTRACT

A cochlear implant system for processing polyphonic pitch includes an electrode array for implanting in a cochlea of a patient. The electrode array includes a first set of electrodes, where each electrode of the first set is for implanting on a first region of the cochlea. The electrode array also includes a second set of electrodes, where each electrode of the second set is for implanting on a second region of the cochlea. The system also includes a sound processor configured to capture a sound signal having polyphonic pitch. For each electrode of the first set and second set, the speech processor generates at least two different modulated frequency signals from the sound signal, such that each of the modulated frequency signals corresponds to a different pitch in the sound signal. The speech processor stimulates the electrode by simultaneously applying the at least two different modulated frequency signals.

24 Claims, 9 Drawing Sheets

(51) Int. Cl.
*A61N 1/05* (2006.01)
*H04R 25/00* (2006.01)

(52) U.S. Cl.
CPC ....... *A61N 1/36192* (2013.01); *H04R 25/505* (2013.01); *H04R 2225/43* (2013.01)

(58) Field of Classification Search
CPC ............ H04R 2225/43; H04R 2225/67; H04R 2430/03; H04R 25/505; H04R 25/606; H04R 25/70
See application file for complete search history.

(56) References Cited

U.S. PATENT DOCUMENTS

| | | |
|---|---|---|
| 8,280,087 B1 | 10/2012 | Bacon et al. |
| 2008/0215332 A1* | 9/2008 | Zeng .................. A61N 1/36038 704/E19.036 |
| 2013/0245717 A1* | 9/2013 | Stohl .................. A61N 1/36038 607/57 |
| 2016/0022991 A1* | 1/2016 | Apoux ............... A61N 1/36038 607/57 |

\* cited by examiner

POLYPHONIC PITCH ENHANCEMENT IN A COCHLEAR IMPLANT

PRIORITY

This application is the national phase entry of International Patent Application No. PCT/US2020/048386, filed Aug. 28, 2020, which claims priority from U.S. Provisional Patent Application No. 62/894,326, filed Aug. 30, 2019, the disclosures of which are incorporated herein by reference in their entirety.

TECHNICAL FIELD

The present invention relates to the processing of polyphonic pitch by cochlear implant systems.

BACKGROUND ART

A normal ear transmits sounds as shown in FIG. 1 through the outer ear 101 to the tympanic membrane (eardrum) 102, which moves the bones of the middle ear 103 (malleus, incus, and stapes) that vibrate the oval window and round window openings of the cochlea 104. The cochlea 104 is a long narrow duct wound spirally about its axis for approximately two and a half turns. It includes an upper channel known as the scala vestibule, a middle chamber known as the scala media, and a lower channel known as the scala tympani, which are connected by the cochlear duct. The cochlea 104 forms an upright spiraling cone with a center called the modiolar where the spiral ganglion cells of the acoustic nerve 113 reside. In response to received sounds transmitted by the middle ear 103, the fluid-filled cochlea 104 functions as a transducer to generate electric pulses which are transmitted to the cochlear nerve 113, and ultimately to the brain.

Hearing is impaired when there are problems in the ability to transduce external sounds into meaningful action potentials along the neural substrate of the cochlea 104. To improve impaired hearing, auditory prostheses have been developed. For example, when the impairment is related to operation of the middle ear 103, a conventional hearing aid or middle ear implant may be used to provide acoustic-mechanical stimulation to the auditory system in the form of amplified sound. Or when the impairment is associated with the cochlea 104, a cochlear implant with an implanted stimulation electrode can electrically stimulate auditory nerve tissue with small currents delivered by multiple electrode contacts distributed along the electrode.

FIG. 1 also shows some components of a typical cochlear implant system, including an external microphone that provides an audio signal input to an external signal processor 111 where various signal processing schemes can be implemented. The processed signal is then converted into a digital data format, such as a sequence of data frames, for transmission via external transmitting coil 107 into the implant receiver 108. Besides receiving the processed audio information, the implant receiver 108 also performs additional signal processing such as error correction, pulse formation, etc., and produces a stimulation pattern (based on the extracted audio information) that is sent through an electrode lead 109 to an implanted electrode array 110. The electrode array 110 includes multiple electrode contacts 112 (also referred to as electrode channels) on its surface that provides selective stimulation of the cochlea 104.

Each of the electrode channels is typically associated with a frequency band, with each electrode contact addressing a group of neurons with an electric stimulation pulse having a charge that is derived from the instantaneous amplitude of the signal envelope within that frequency band. Current cochlear implant coding strategies map the different sound frequency channels onto different locations within the cochlea. FIG. 2 shows one example of the processing of a signal using the cochlear implant stimulation (CIS) stimulation strategy. The top of FIG. 2 shows the sound pressure characteristics of a spoken "A" (/ay/) at a sound level of 67.2 dB. The middle waveform in FIG. 2 shows a normal healthy auditory system response. The bottom waveform in FIG. 2 shows a neural response of the auditory nerve fibers under CIS stimulation.

FIG. 3 shows various functional blocks in a signal processing arrangement for producing electrode stimulation signals to electrode contacts in an implanted cochlear implant array according to a typical hearing implant system. A pseudo code example of such an arrangement can be set forth as:

```
Input Signal Preprocessing:
    BandPassFilter (input_sound, band_pass_signals)
Envelope Extraction:
    BandPassEnvelope (band_pass_signals, band_pass_envelopes)
Stimulation Timing Generation:
    TimingGenerate (band_pass_signals, stim_timing)
Pulse Generation:
    PulseGenerate (band_pass_envelopes, stim_timing, out_pulses)
```

The details of such an arrangement are set forth in the following discussion.

In the signal processing arrangement shown in FIG. 3, the initial input sound signal is produced by one or more sensing microphones, which may be omnidirectional and/or directional. Preprocessor Filter Bank 301 pre-processes this input sound signal with a bank of multiple parallel band pass filters (e.g. Infinite Impulse Response (IIR) or Finite Impulse Response (FIR)), each of which is associated with a specific band of audio frequencies, for example, using a filter bank with 12 digital Butterworth band pass filters of 6th order, Infinite Impulse Response (IIR) type, so that the acoustic audio signal is filtered into some K band pass signals, $U_1$ to $U_K$ where each signal corresponds to the band of frequencies for one of the band pass filters. Each output of sufficiently narrow CIS band pass filters for a voiced speech input signal may roughly be regarded as a sinusoid at the center frequency of the band pass filter which is modulated by the envelope signal. This is also due to the quality factor ($Q \approx 3$) of the filters. In case of a voiced speech segment, this envelope is approximately periodic, and the repetition rate is equal to the pitch frequency. Alternatively and without limitation, the Preprocessor Filter Bank 301 may be implemented based on use of a fast Fourier transform (FFT) or a short-time Fourier transform (STFT).

Based on the tonotopic organization of the cochlea, each electrode contact in the scala tympani typically is associated with a specific band pass filter of the Preprocessor Filter Bank 301. The Preprocessor Filter Bank 301 also may perform other initial signal processing functions such as and without limitation automatic gain control (AGC) and/or noise reduction and/or wind noise reduction and/or beamforming and other well-known signal enhancement functions. An example of pseudocode for an infinite impulse response (IIR) filter bank based on a direct form II transposed structure is given by Fontaine et al., *Brian Hears: Online Auditory Processing Using Vectorization Over Chan-*

*nels*, Frontiers in Neuroinformatics, 3011; incorporated herein by reference in its entirety.

The band pass signals $U_1$ to $U_K$ (which can also be thought of as electrode channels) are output to a Stimulation Timer 306 that includes an Envelope Detector 302 and Fine Structure Detector 303. The Envelope Detector 302 extracts characteristic envelope signals outputs $Y_1, \ldots, Y_K$ that represent the channel-specific band pass envelopes. The envelope extraction can be represented by $Y_k = LP(|U_k|)$, where $|\cdot|$ denotes the absolute value and $LP(\cdot)$ is a low-pass filter; for example, using 12 rectifiers and 12 digital Butterworth low pass filters of 2nd order, IIR-type. Alternatively, the Envelope Detector 302 may extract the Hilbert envelope, if the band pass signals $U_1, \ldots, U_K$ are generated by orthogonal filters.

Optionally, the Fine Structure Detector 303 functions to obtain smooth and robust estimates of the instantaneous frequencies in the signal channels, processing selected temporal fine structure features of the band pass signals $U_1, \ldots, U_K$ to generate stimulation timing signals $X_1, \ldots, X_K$. The band pass signals $U_1, \ldots, U_k$ can be assumed to be real valued signals, so in the specific case of an analytic orthogonal filter bank, the Fine Structure Detector 303 considers only the real valued part of $U_k$. The Fine Structure Detector 303 is formed of K independent, equally-structured parallel sub-modules.

The Pulse Generator 304 applies a patient-specific mapping function—for example, using instantaneous nonlinear compression of the envelope signal (map law)—that is adapted to the needs of the individual cochlear implant user during fitting of the implant in order to achieve natural loudness growth. The Pulse Generator 304 may apply logarithmic function with a form-factor C as a loudness mapping function, which typically is identical across all the band pass analysis channels. In different systems, different specific loudness mapping functions other than a logarithmic function may be used, with just one identical function is applied to all channels or one individual function for each channel to produce the electrode stimulation signals. The electrode stimulation signals typically are a set of symmetrical biphasic current pulses. The Implant 305 receives the output from the Pulse Generator 304.

Cochlear implant users often have difficulties with the auditory task of music perception. Most music is polyphonic, comprising multiple simultaneous pitches. Cochlear implant users lack an accurate perception of pitch. Cochlear implant users thus cannot perceive the different pitches simultaneously occurring in music, but rather perceive these separate pitches as a single pitch. Current cochlear implants do not account for the possible occurrence of polyphony pitch when processing the audio information of users.

Pitch is the psychophysical correlate of a sound's fundamental frequency, which can be used to order sounds on a frequency scale from low to high. In the normal hearing ear, the cochlea 104 discriminates and encodes pitch using two fundamental mechanisms. Through these two mechanisms, the normal hearing ear perceives polyphony pitch. The first mechanism is called place pitch, which activates the regions of the cochlea 104 most responsive to the frequency of an incoming pitch signal. Place pitch is based on the mechanical properties of the basilar membrane and the tonotopy of the cochlea.

The basilar membrane is located between the scala media and the scala tympani of the cochlea 104. Auditory receptor cells (called hair cells) are arranged along the tonotopic gradient of the cochlea 104 and activated by simulation from the basilar membrane. The hair cells are organized into three rows of outer hair cells (OHCs) and one row of inner hair cells (IHCs). The OHCs modify input signals by augmenting basilar membrane motion. The modified input signals are transduced to the IHCs, which causes a pulse train that transmits the modified input signals along the auditory nerve to the brainstem. The IHCs have characteristic frequencies to which they are tuned based on their location on the cochlea 104. High frequency signals activate the basal regions of the cochlea 104, whereas low frequency signals activate the apical regions of the cochlea 104. This place-frequency transformation is commonly called tonotopy of the cochlea. In place pitch, the basilar membrane of the cochlea acts as a frequency analyzer and activates the hair cells that are specifically tuned to the frequency of an input pitch signal.

The second mechanism of a normal hearing ear is called rate pitch, which phase locks the firing rate of auditory neurons (or auditory nerve fibers) to the frequency of the input pitch signal. In this way, spikes in firing of the auditory neurons correspond to the periodic peaks in the amplitude of the input signal. Phase locking to the input signal is a result of the cyclic increase and decrease of glutamate release from the IHC caused by the alternating current receptor on the IHC member. The brain combines the firings of auditory neurons caused by an input signal into a pattern that resembles the characteristic frequency of the input signal.

In a cochlear implant user, the hairs cells of the cochlea 104 may be damaged, thereby impairing the place pitch and rate pitch mechanisms of the cochlea 104. Current cochlear implants do not apply processing strategies to specifically address impairments in the place pitch and rate pitch mechanisms of a user.

SUMMARY OF THE EMBODIMENTS

Various embodiments of the present invention are directed to a cochlear implant system for processing polyphonic pitch. The system includes an electrode array for implanting in a cochlea of a patient. The electrode array includes a first set of electrodes, each electrode of the first set for implanting on a first region of the cochlea. The electrode array also includes a second set of electrodes, each electrode of the second set for implanting on a second region of the cochlea. The system also includes a sound processor configured to capture a sound signal having polyphonic pitch. For each electrode of the first set and the second set, the speech processor generates at least two different modulated frequency signals from the sound signal. Each modulated frequency signal corresponds to a different pitch in the sound signal. The speech processor stimulates the electrode by simultaneously applying the at least two different modulated frequency signals to the electrode.

In some embodiments, the sound processor is configured to apply the at least two different modulated frequency signals to the electrode in an interleaved arrangement. In some embodiments, each electrode of the first set of electrodes and the second set of electrodes is configured for implantation on the cochlea at least at a minimum spatial distance from each other electrode of the first set and the second set. In example embodiments, the sound processor is configured to generate the modulated frequency signals such that a same ratio exists between the two different modulated frequency signals of a given electrode of the first set of electrodes and the two different modulated frequency signals of a given electrode of the second set of electrodes. In some embodiments, the sound processor is configured to generate: the at least two modulated signals for each of the first set of electrodes as low frequency signals, and the at least two modulated signals for each of the second set of electrodes as high frequency signals, wherein the high frequency signals are at a higher frequency relative to the low frequency signals.

In example embodiments, the sound processor is configured to select fundamental frequencies for the modulation signals. The selection by the sound processor includes one or more of the following. The selection may include a fitting assessment of specific electrode and stimulation rate combinations for a fundamental frequency range. The assessment being performed by: (i) varying the specific electrode and stimulating rate combinations, and (ii) identifying, by the patient, a desired combination of electrodes and stimulation rates of the perceived harmonicity for each fundamental frequency. The selection may include execution of a running coding strategy that selects the fundamental frequencies by performing an extraction process on the sound signal using periodicity analysis. In some example embodiments, the coding strategy selects the fundamental frequencies based on extracting: (i) a number of fundamental frequencies in the sound signal, (ii) a frequency value of each of the fundamental frequencies, and (iii) a frequency range of the electrodes.

In some embodiments, the first set of electrodes is located in a more apical region of the cochlea relative to the second set of electrodes, which is located in a more basal region of the cochlea. In some embodiments, at least one of the first set of electrodes and the second set of electrodes includes at least two electrodes. In some embodiments, the at least two different modulated frequency signals are fundamental frequencies.

Various embodiments of the present invention are directed to a method of processing polyphonic pitch by a cochlear implant system associated with a patient. The cochlear implant system including an electrode array including a first set of electrodes for implanting on a first region of the cochlea of the patient, and a second set of electrodes for implanting on a second region of the cochlea of the patient. The method also includes capturing a sound signal having polyphonic pitch. For each electrode of the first set and the second set, the method includes generating at least two different modulated frequency signals from the sound signal. Each modulated frequency signal corresponds to a different pitch in the sound signal. The method further includes stimulating the electrode by simultaneously applying the at least two different modulated frequency signals to the electrode.

In some embodiments, the method applies the at least two different modulated frequency signals to the electrode in an interleaved arrangement. In some embodiments, each electrode of the first set of electrodes and the second set of electrodes is configured for implantation on the cochlea at least at a minimum spatial distance from each other electrode of the first set and the second set. In example embodiments, the modulated frequency signals are generated such that a same ratio exists between the two different modulated frequency signals of a given electrode of the first set of electrodes and the two different modulated frequency signals of a given electrode of the second set of electrodes. In some embodiments, the at least two modulated signals for each of the first set of electrodes are generated as low frequency signals, and the at least two modulated signals for each of the second set of electrodes are generated as high frequency signals, wherein the high frequency signals are at a higher frequency relative to the low frequency signals.

In example embodiments, the method further includes selecting the fundamental frequencies for the modulation signals by one or more of the following. The method may including fitting frequency relations of the patent by assessing specific electrode and stimulation rate combinations for a fundamental frequency range. The assessment being performed by: (i) varying the specific electrode and stimulating rate combinations, and (ii) identifying, by the patient, a combination perceived harmonic for each fundamental frequency. The method further includes executing a running coding strategy that selects the fundamental frequencies by performing an extraction process on the sound signal using periodicity analysis. In some example embodiments, the method further includes defining, by the running coding strategy, the fundamental frequencies based on extracting: (i) a number of fundamental frequencies in the sound signal, (ii) a frequency value of each of the fundamental frequencies, and (iii) a frequency range of the electrodes.

In some embodiments, the first set of electrodes is located in a more apical region of the cochlea relative to the second set of electrodes, which is located in a more basal region of the cochlea. In some embodiments, at least one of the first set of electrodes and the second set of electrodes includes at least two electrodes. In some embodiments, the at least two different modulated frequency signals are fundamental frequencies.

Embodiments of the present invention are directed to a non-transitory tangible computer program product in a computer-readable medium for processing polyphonic pitch by stimulating electrodes of an electrode array in a cochlear implant system associated with a patient. The electrode array including a first set of electrodes for implanting on a first region of the cochlea, and a second set of electrodes for implanting on a second region of the cochlea. The product includes program code for capturing a sound signal having polyphonic pitch. For each electrode of the first set and the second set, the product includes program code for generating at least two different modulated frequency signals from the sound signal. Each modulated frequency signal corresponding to a different pitch in the sound signal. The product also include program code for stimulating the electrode by simultaneously applying the at least two different modulated frequencies to the electrode.

In some embodiments, the at least two different modulated frequency signals are applied to the electrode in an interleaved arrangement. In some embodiments, each electrode of the first set of electrodes and the second set of electrodes is configured for implantation on the cochlea at least at a minimum spatial distance from each other electrode of the first set and the second set. In example embodiments, the modulated frequency signals are generated such that a same ratio exists between the two different modulated frequency signals of a given electrode of the first set of electrodes and the two different modulated frequency signals of a given electrode of a second set of electrodes. In some embodiments, the at least two modulated signals for each of the first set of electrodes are generated as low frequency signals, and the at least two modulated signals for each of the second set of electrodes are generated as high frequency signals, wherein the high frequency signals are at a higher frequency relative to the low frequency signals.

In example embodiments, the product further includes program code for selecting fundamental frequencies for the modulation signals. The selecting includes one or more of the following. The selecting may include a fitting assessment of specific electrode and stimulation rate combinations for a fundamental frequency range. The assessment being performed by: (i) varying the specific electrode and stimulating rate combinations, and (ii) identifying, by the patient, a combination perceived harmonic for each fundamental frequency. The selecting may include executing a running coding strategy that selects the fundamental frequencies by performing an extraction process on the sound signal using periodicity analysis. In some example embodiments, the product may include program code for selecting, by the running coding strategy, the fundamental frequencies based on extracting: (i) a number of fundamental frequencies in the sound signal, (ii) a frequency value of each of the fundamental frequencies, and (iii) a frequency range of the electrodes.

In some embodiments, the first set of electrodes is located in a more apical region of the cochlea relative to the second set of electrodes, which is located in a more basal region of the cochlea. In some embodiments, at least one of the first set of electrodes and the second set of electrodes includes at least two electrodes. In some embodiments, the at least two different modulated frequency signals are fundamental frequencies.

BRIEF DESCRIPTION OF THE DRAWINGS

The foregoing features of embodiments will be more readily understood by reference to the following detailed description, taken with reference to the accompanying drawings, in which.

DETAILED DESCRIPTION OF SPECIFIC EMBODIMENTS

Embodiments of the present invention are direct to a strategy of encoding polyphonic pitch of an incoming audio signal in the stimulation of electrodes of an implanted electrode array of a cochlea implant system. The embodiments select fundamental frequencies of pitch from the incoming audio signal based on patient-specific mappings of electrodes to stimulation rates. The embodiments adjust stimulation rates of the electrodes in the patient-specific mappings by modulating the amplitude of the pulse current on the electrodes with different sinusoidally amplitude modulated frequencies simultaneously in an interleaved arrangement.

Figure 4:
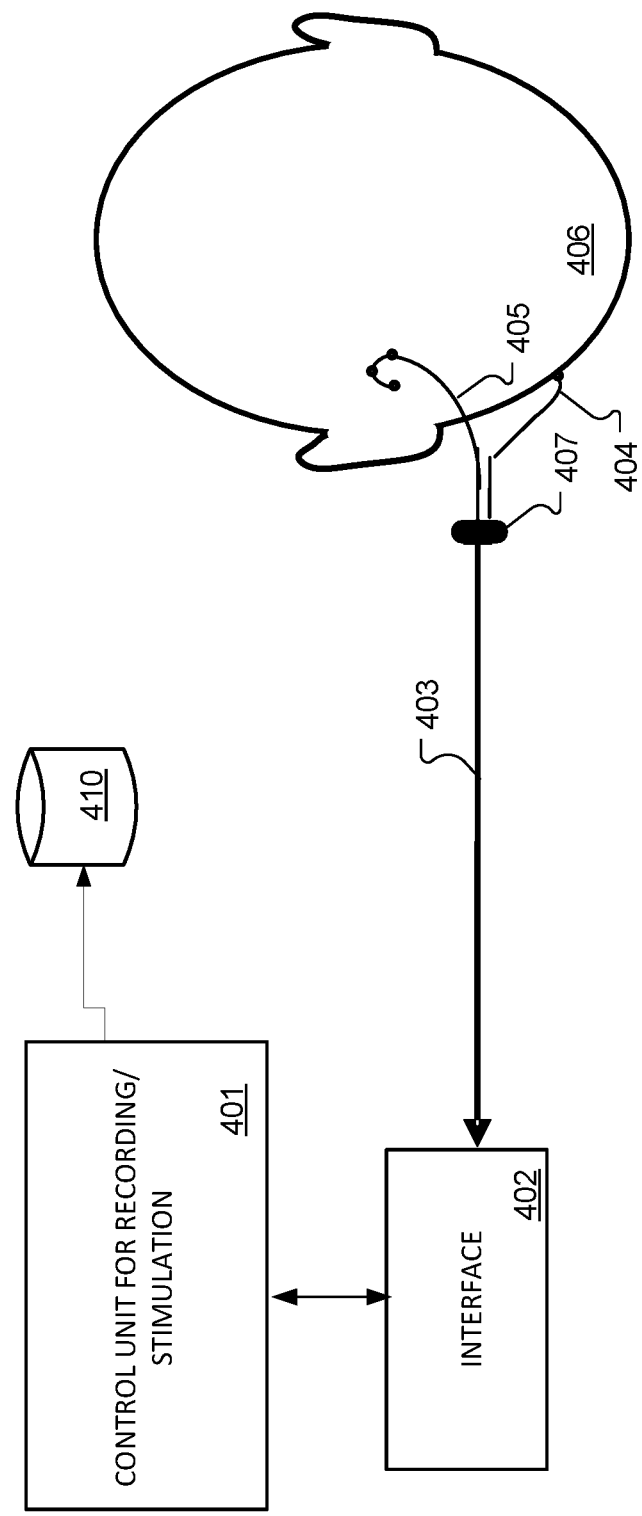
FIG. 4 shows a block diagram of a cochlear implant fitting system, according to an embodiment of the present invention.

FIG. 4 shows a block diagram of a cochlear implant fitting system, according to an embodiment of the present invention. Control Unit 401 for Recording and Stimulation, for example, a Med-El Maestro Cochlear Implant (CI) system, generates stimulation signals and analyzes response measurements. Connected to the Control Unit 401 is an Interface Box 402, for example, a Diagnostic Interface System such as the DIB II conventionally used with the Maestro CI system that formats and distributes the input and output signals between the Control Unit 401 and the system components implanted in the Patient 406. For example, as shown in FIG. 4, there may be an Interface Lead 403 connected at one end to the Interface Box 402 and at the other end having Electrode Plug 407 that then divides into a Cochlear Implant Electrode Array 405 (and optionally an Extra-Cochlear Ground Electrode 404). For a range of fundamental frequencies (F0s), the Control Unit 401 is configured to fit electrodes of the Cochlear Implant Electrode Array 405 to stimulation rates that provide the most harmonic perception of sound to a subject patient. The Control Unit 401 includes a fitting processor with at least one hardware implanted processor device and is controlled by software instructions to perform the fitting process including delivering to the electrodes a test stimulation sequence which is at a variable stimulation rate over time. The Control Unit 401 is coupled to a database 410 for storing the results of the fitting process.

Figure 5:
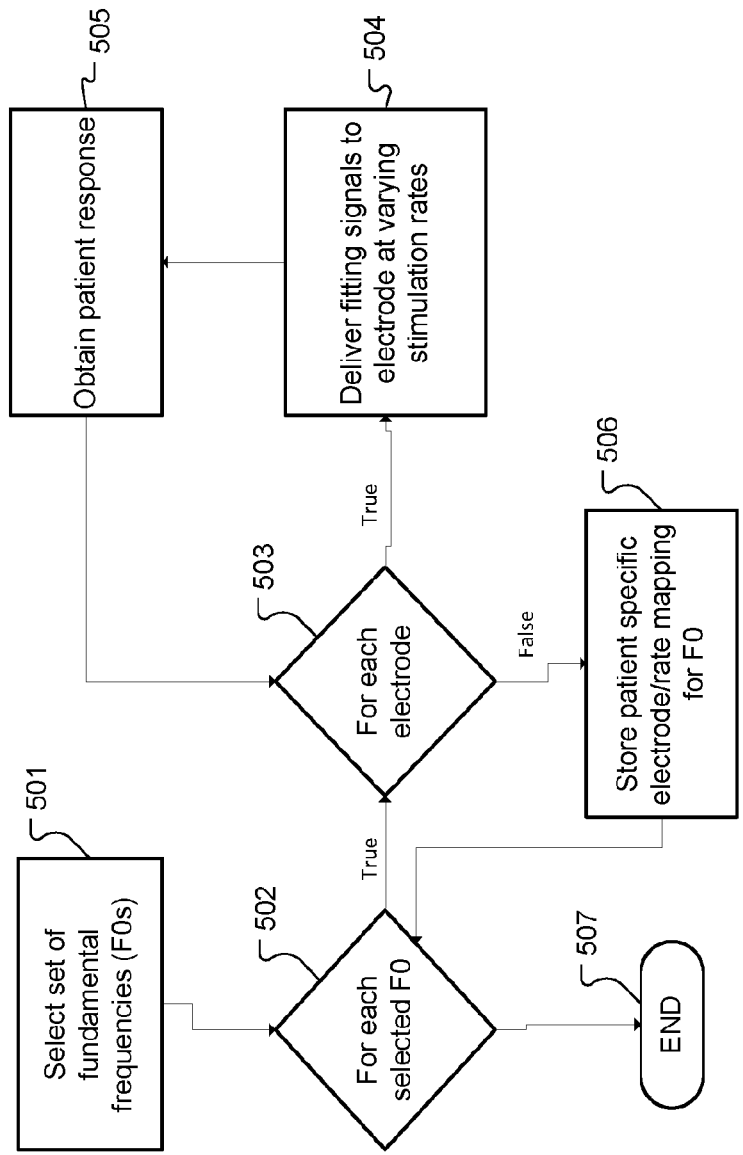
FIG. 5 shows various logical steps in a fitting process, according to an embodiment of the present invention.

More specifically, the fitting system depicted in FIG. 4 is operated to iteratively fit electrodes to stimulation rates for each of a set of fundamental frequencies following the basic logical steps shown in the method of FIG. 5. First, at step 501, a set of fundamental frequencies is selected from a fundamental frequency range (e.g., 100 to 600 Hz) specific to the subject patient. Next, for each of the fundamental frequencies in the set, step 502, a set of electrodes is iteratively fit. For example, the set of electrodes may be all or some of the electrodes sequentially starting from, for example, an apical end of the electrode array back along the length of the electrode array. Or the set of electrodes may be all or some of the electrodes fit in a non-linear order along the electrode array. Or the set of electrodes may be an alternating sequence of every other electrode contact along at least a portion of the length of the electrode array.

For each of the fitting electrodes, iteratively, step 503, fitting stimulation signals are delivered to the fitting electrode at varying stimulation rates, step 504. Step 505 obtains responses, which may include subjective and/or objective response measurements, from the subject patient to the fitting stimulation signals at the varying stimulation rates. For example, the subject patient may scale the pleasantness or harmonicity of the perceived sound from the fitting stimulation signals at each of the varying rates. Steps 503-505 are performed for each fitting electrodes.

Based on the subject patient responses, step 506 defines a patient-specific fit map of one or more fitting electrode and stimulates rate combinations for the fundamental frequency. For example, the patient-specific fit mapping may define the one or more fitting electrode and stimulation rate combinations that provide the most harmonic perception of sound to the subject patient at the fundamental frequency. Steps 502-506 are performed for each fundamental frequency of the selected set of fundamental frequencies. The method ends at step 507.

Figure 1:
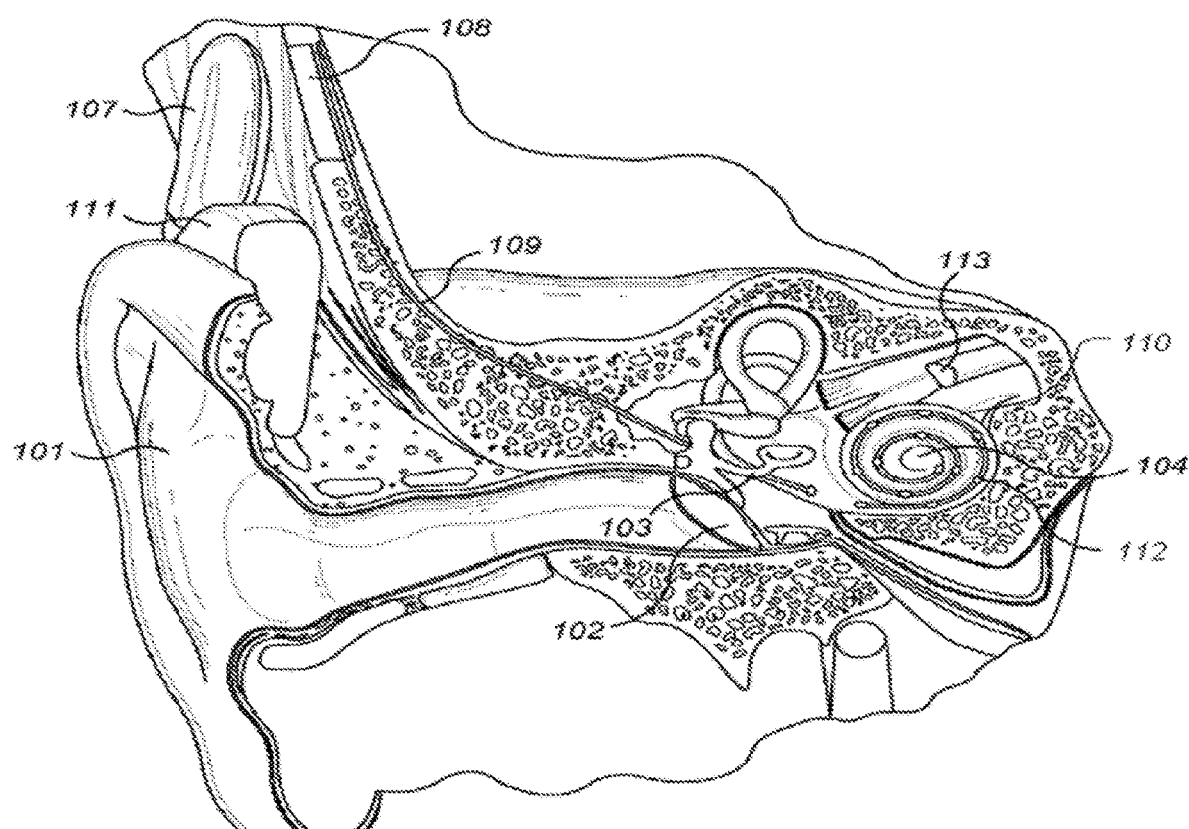
FIG. 1 shows anatomical structures of a typical human ear with a cochlear implant system.
Figure 2:
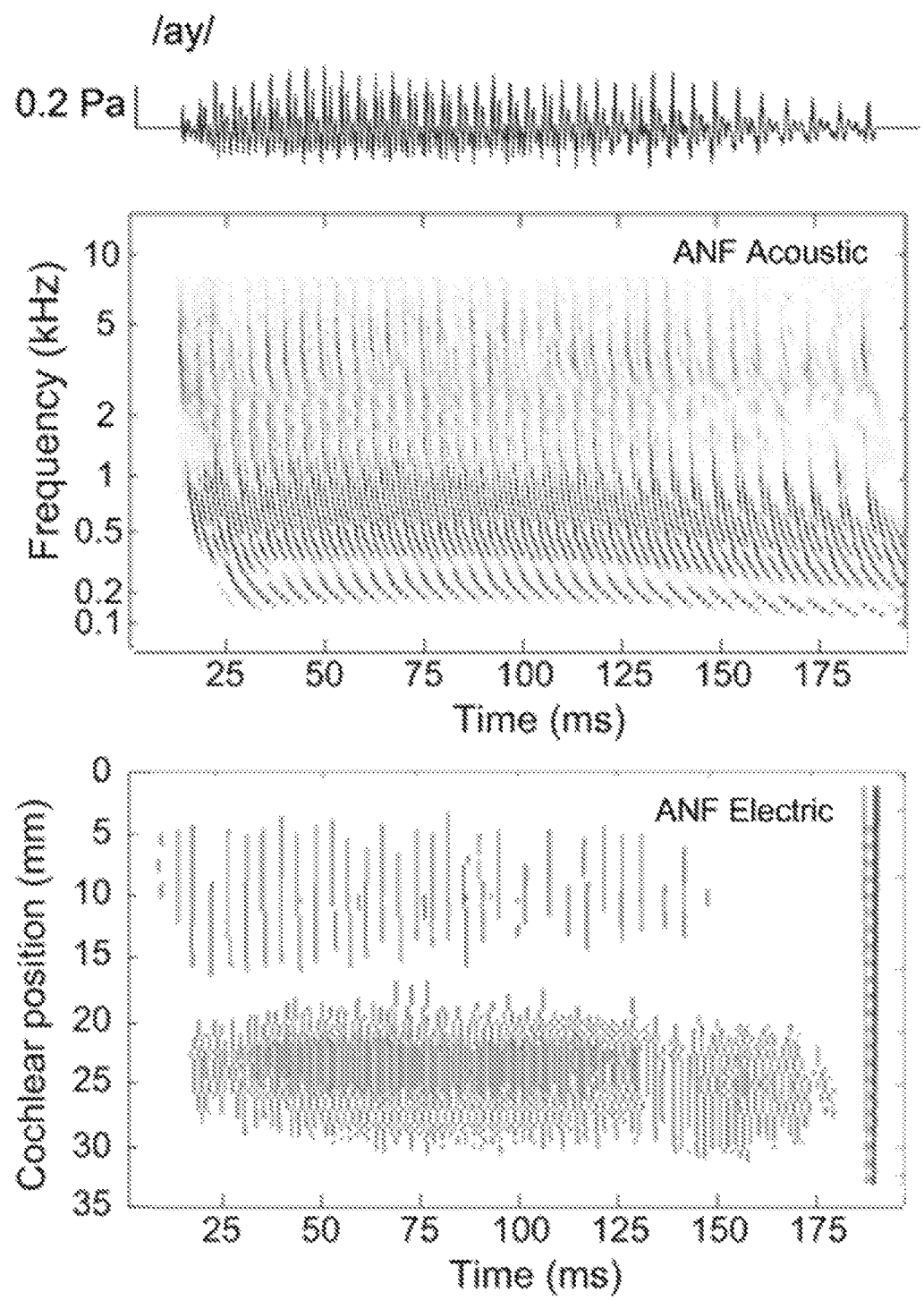
FIG. 2 shows an example of signal processing using the cochlear implant stimulation strategy.
Figure 3:
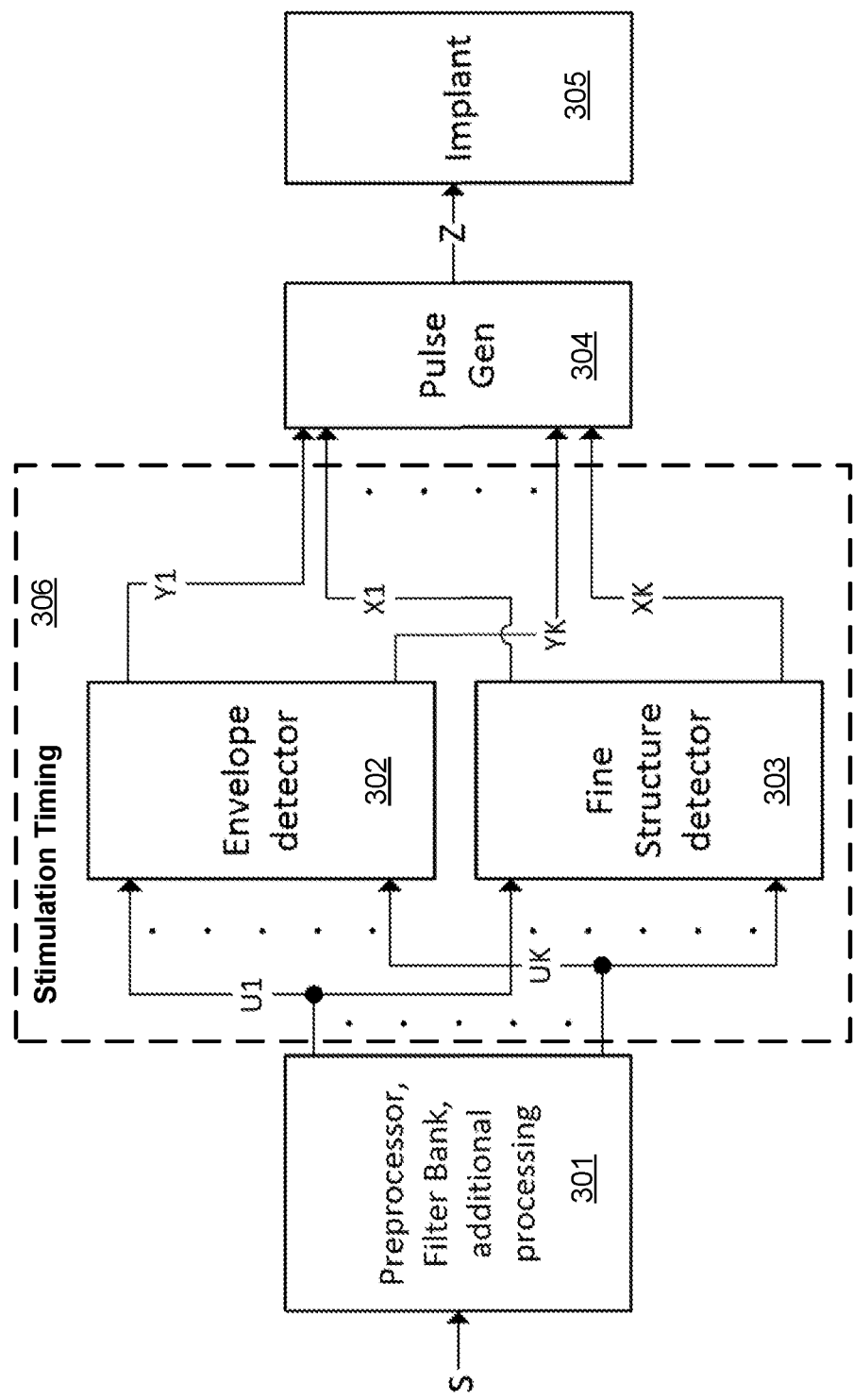
FIG. 3 shows various functional blocks in a signal processing arrangement for a typical cochlear implant system.
Figure 6:
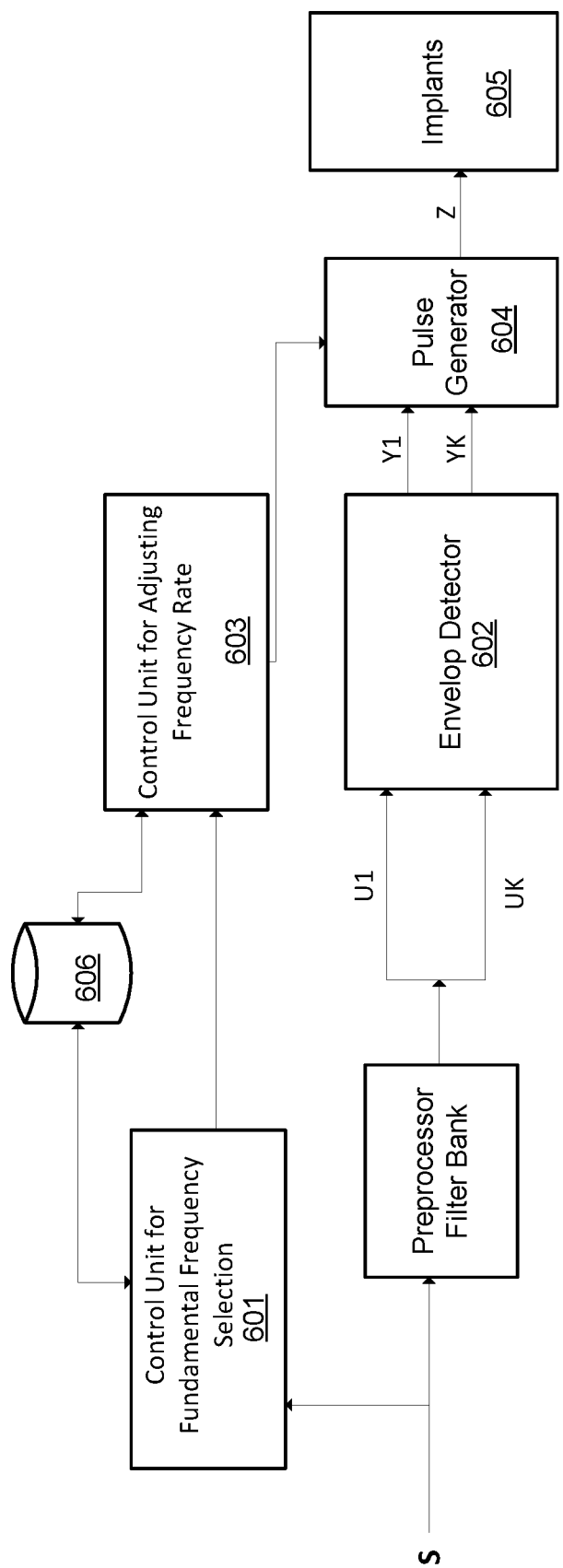
FIG. 6 shows various functional blocks in a signal processing arrangement for a cochlear implant system, according to an embodiment of the present invention.

FIG. 6 shows various functional blocks in a signal processing arrangement for a cochlear implant system according to an embodiment of the present invention. FIG. 6 is an adaptation of the signal processing arrangement of FIG. 3 for processing polyphonic audio signals. Control Unit 601 for Fundamental Frequency Selection is added to the signal processing arrangement to extract and select a set of fundamental frequencies of pitch from an incoming polyphonic audio signal. Control Unit 601 retrieves from database 606 the patient-specific electrode/rate mappings for fundamental frequencies, and selects the set of fundamental frequencies based on the patient specific mappings. In embodiments, the patient-specific electrode/rate mappings were generated using the cochlear implant fitting system of FIG. 4 and method of FIG. 5.

Control Unit 603 for Adjusting Stimulation Rate is added to the signal processing arrangement coupled to Control Unit 601 and database 606. Control Unit 603 receives the selected set of fundamental frequencies from Control Unit 601. Control Unit 603 adjusts the stimulation rate of certain electrodes of the implanted electrode array (Implants) 605 over time according to the patient-specific mapping to enhance the selected fundamental frequencies. In particular, a rate pitch sensation can be created at the Pulse Generator 604 by modulating the amplitude of the current pulses to the certain electrodes in accordance with the corresponding stimulation rates in the mapping. Amplitude modulated rate pitch sensations can also be created as the Envelop Detector 602 extracts the envelops of the signal and maps the envelops on the corresponding electrodes.

Figure 7:
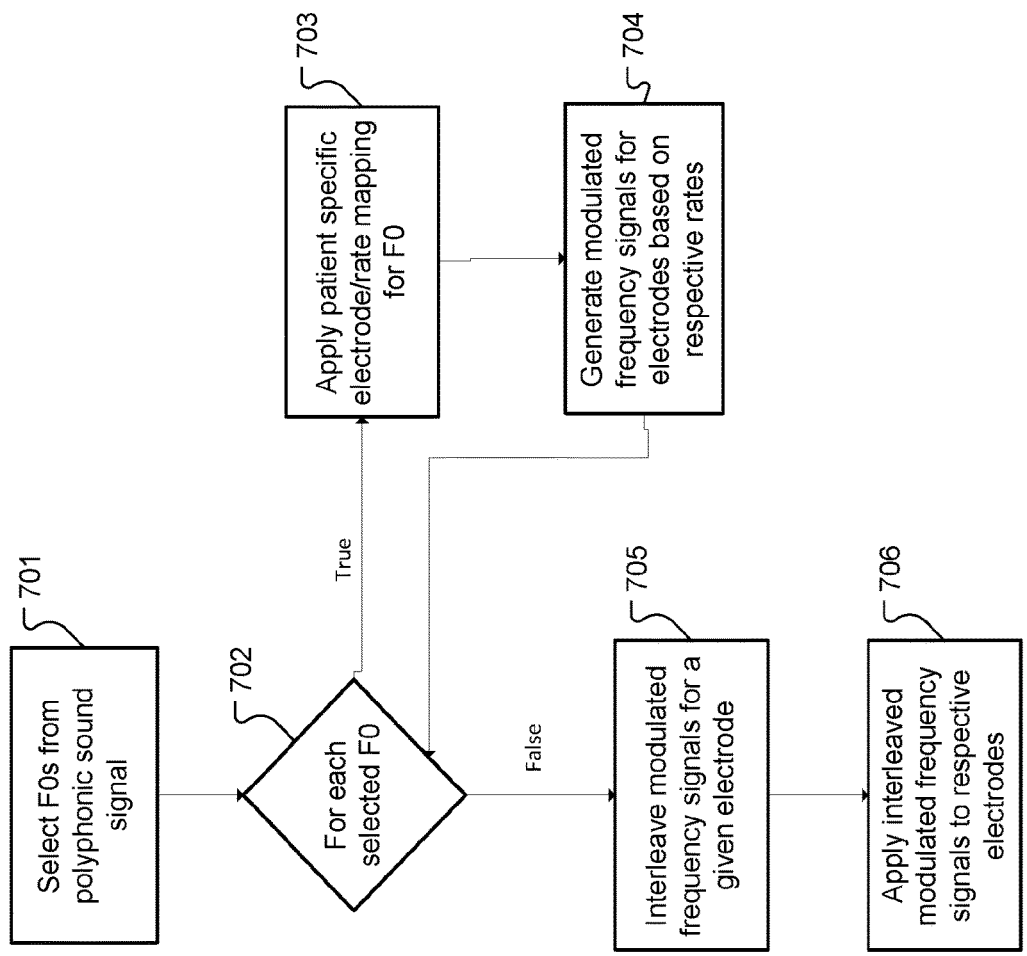
FIG. 7 shows various logical steps in a polyphonic pitch encoding process, according to an embodiment of the present invention.

More specifically, the fitting system depicted in FIG. 6 is operated to encode a set of fundamental frequencies of pitch from a polyphonic audio signal following the basic logical steps shown in the method of FIG. 7. First, at step 701, a set of fundamental frequencies of pitch is selected from an incoming polyphonic audio signal. Step 701 may extract related information from the audio signal, including the number of fundamental frequencies in the signal, the value of each fundamental frequency, and the frequency range in which each fundamental frequency is located. The extraction can be performed by the use of a periodicity analyzer applying methods such as autocorrelation and cepstrum analysis. Step 701 may also retrieve the patient-specific electrode to stimulation rate mappings for fundamental frequencies. Based on this information, step 701 selects the set of fundamental frequencies from the signal specific to the patient. Step 701 may select the set of fundamental frequencies such that the corresponding patient-specific mappings include a particular placement of electrodes on the apical region and on the basal regions of the cochlea. Further, the set of fundamental frequencies may be selected such that the corresponding patient-specific mappings include the basal region electrodes and the apical region electrodes placed at a minimum spatial distance from other electrodes implanted on the cochlea.

Next, step 702, for each of the fundamental frequencies in the set, at step 703 applies the electrode and stimulation rate mapping for that fundamental frequency. In particular, step 703 enhances the fundamental frequency at the electrode in the mapping according to the stimulation rate in the mapping. To enhance the fundamental frequency, step 704 creates a rate pitch sensation according to that fundamental frequency by modulating the amplitude of current of pulse (pulse train) on the electrode with a sine wave at a modulation frequency. The rate of pulses of the pulse train is called carrier rate. This type of pitch encoding to create temporal pitch is called "sinusoidal amplitude modulation". By using a high rate carrier pulse train, step 704 can provide a polyphonic pitch cue to convey pitch sensation on the electrode. Steps 702-704 are performed for each selected fundamental frequency.

To create the polyphonic pitch cue, for example, sinusoidal amplitude modulation (SAM) may be applied to a carrier pulse train of an electrode using the equation: $SAM(t)=f(t)+d \times \sin(2\pi f_m \times t + 3\pi/2)$, where f(t) is the unmodulated pulse train at, for example 5000 pps, presented at the threshold level and d is the depth of the modulation. The factor $F_m$ is the modulation frequency and may have a starting phase of $3\pi/2$. The maxima and minima of the SAM corresponded to the subject's maximal comfort level and the threshold level as measured by the unmodulated pulse train.

Polyphonic place pitch can be created by modulating the amplitude of the pulse current on the electrodes of the mappings corresponding to the selected fundamental frequencies simultaneously with the same sinusoidally amplitude modulated frequency. The polyphonic place pitch is made stronger when the distances between the electrodes are increased. Polyphonic rate pitch is created by modulating the amplitude of the pulse current on the electrodes of the mappings with different sinusoidally amplitude modulated frequencies simultaneously. To do this, the carrier rate on an electrode has to be increased, e.g., to 10,000 pps, and the modulated current pulses for each carrier, e.g., 5,000 pps, are then presented interleaved on the electrode. The polyphonic place pitch is made stronger when the differences between the different sinusoidally amplitude modulated frequencies are increased. In example embodiments, step 704 generates the sinusoidally amplitude modulated frequencies such that a same ratio exists between the different modulated frequencies of a given apical region electrode and the different modulated frequencies of a given basal region electrode. In some embodiments, step 704 generates the amplitude modulated frequencies for apical electrodes as low frequency signals, and the amplitude modulated frequencies for basal electrodes as high frequency signals.

Step 705 interleaves the different amplitude modulated signals generated for a given electrode. Step 706 applies the amplitude modulated signals simultaneously to the current pulse of the respective electrodes.

Figure 8:
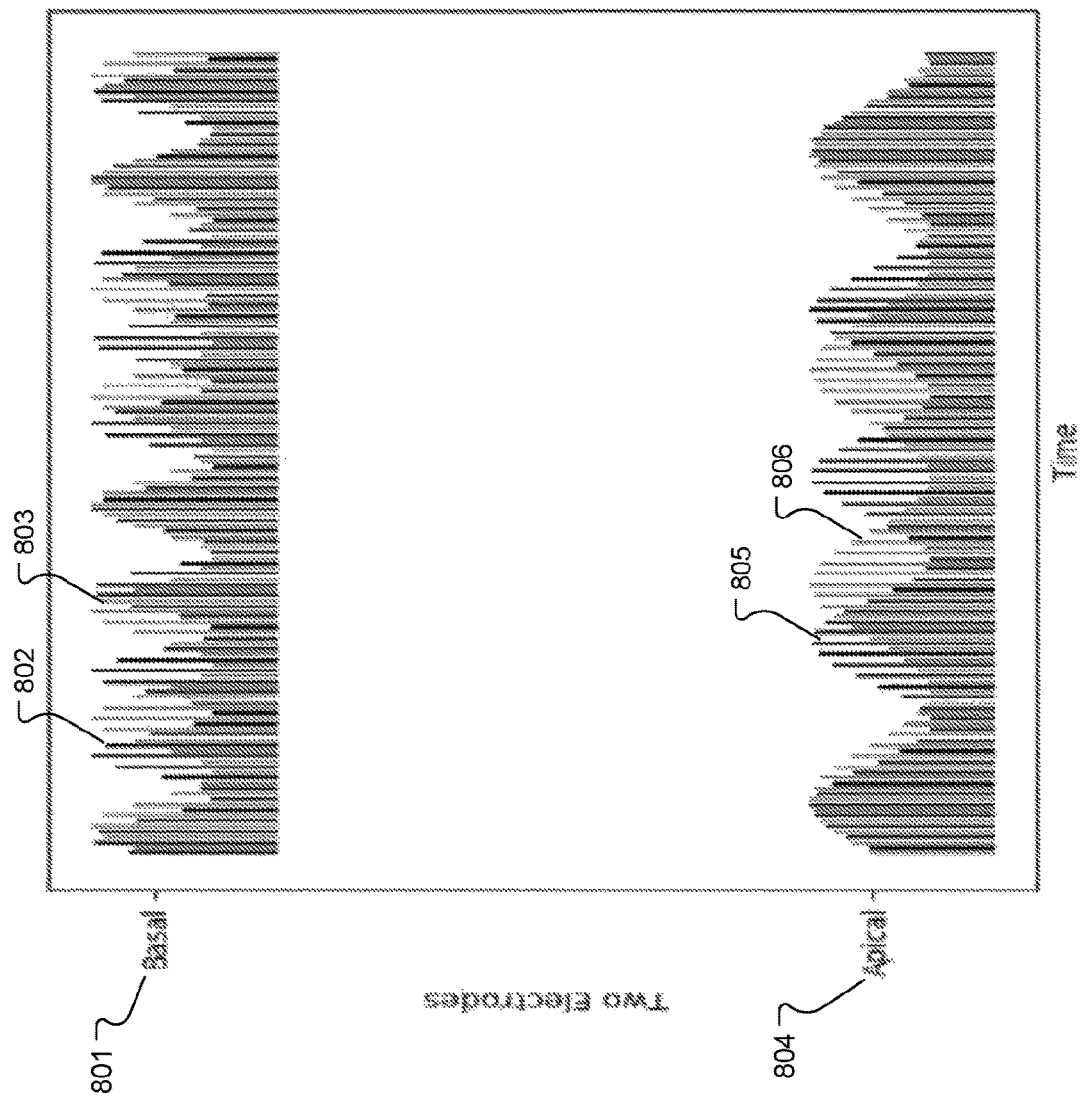
FIG. 8 shows an example of signal processing using the cochlear implant stimulation strategy of FIG. 7.

FIG. 8 shows an example of signal processing using the cochlear implant stimulation strategy of FIG. 7. At the top of FIG. 8, for an electrode 801 on the basal region, the signal processing generates, interleaves, and applies two different sinusoidally amplitude modulated frequencies 802, 803 to the current pulse of the electrode 801. At the bottom of FIG. 8, for an electrode 804 on the apical region, the signal processing generates, interleaves, and applies two different sinusoidally amplitude modulated frequencies 805, 806 to the current pulse of the electrode 804.

Figure 9:
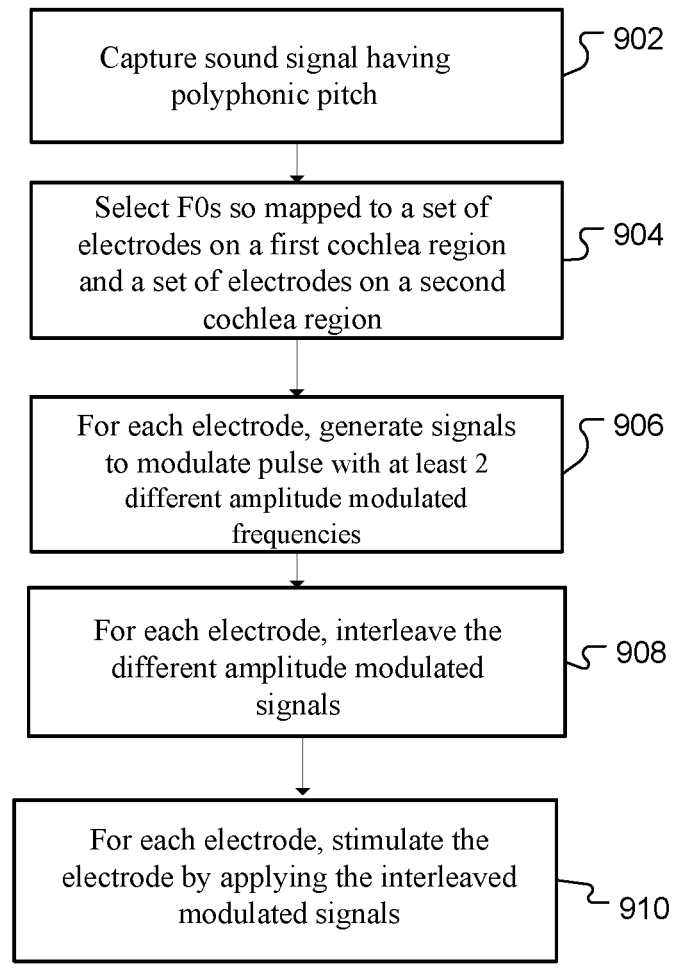
FIG. 9 shows various logical steps in a polyphonic pitch encoding process of at least two modulated signals on a first set of electrodes and a second of electrodes located in a more basal region of the cochlea relative to the first set of electrode, according to an embodiment of the present invention.

More specifically, the signal processing depicted in FIG. 8 is performed following the basic logical steps shown in the method of FIG. 9. Step 902 captures an incoming sound signal having polyphonic pitch. A set of fundamental frequencies of pitch are selected from the polyphonic sound signal based on patient-specific electrode and stimulation rate mappings for the fundamental frequencies. To create a polyphonic rate pitch sensation from the sound signal, step 904 selects the fundamental frequencies, such that they are mapped to a first set of electrode on a first region of the cochlea and a second set of electrodes on a second region of the cochlea. In some embodiments, the first set electrodes may be located in a more apical region of the cochlea relative to the second set of electrodes, which is located in a more basal region of the cochlea. In some embodiments, one of, or both of, the first set of electrodes and the second set of electrodes may include at least two electrodes.

For each of the mapped electrodes, step 906 generates signals to modulate the pulse current on the electrode with at least two different sinusoidally amplitude modulated frequencies simultaneously. For each of the electrodes, step 908 interleaves the at least two different amplitude modulated signals generated for the electrode. For each of the electrodes, step 910 stimulates the electrode by applying the interleaved amplitude modulated signals to the electrode.

Various embodiments of the present invention may be characterized by the potential claims listed in the paragraphs following this paragraph (and before the actual claims provided at the end of this application). These potential claims form a part of the written description of this application. Accordingly, subject matter of the following potential claims may be presented as actual claims in later proceedings involving this application or any application claiming priority based on this application. Inclusion of such potential claims should not be construed to mean that the actual claims do not cover the subject matter of the potential claims. Thus, a decision to not present these potential claims in later proceedings should not be construed as a donation of the subject matter to the public.

The embodiments of the invention described above are intended to be merely exemplary; numerous variations and modifications will be apparent to those skilled in the art. All such variations and modifications are intended to be within the scope of the present invention as defined in any appended claims.

What is claimed is:

1. A cochlear implant system for processing polyphonic pitch, the system comprising:
    an electrode array for implanting in a cochlea of a patient, the electrode array including:
        a first set of electrodes, each electrode of the first set for implanting on a first region of the cochlea, and
        a second set of electrodes, each electrode of the second set for implanting on a second region of the cochlea; and
    a sound processor configured to:
        capture a sound signal having polyphonic pitch; and
        for each electrode of the first set and the second set:
            generate at least two different modulated frequency signals from the sound signal, each modulated frequency signal corresponding to a different pitch in the sound signal, and
            stimulate the electrode by simultaneously applying the at least two different modulated frequency signals to the electrode,
        wherein the sound processor is configured to apply the at least two different modulated frequency signals to the electrode in an interleaved arrangement.

2. The system according to claim 1, wherein each electrode of the first set of electrodes and the second set of electrodes is configured for implantation on the cochlea at least at a minimum spatial distance from each other electrode of the first set and the second set.

3. The system according to claim 1, wherein the sound processor is configured to generate the modulated frequency signals such that a same ratio exists between the two different modulated frequency signals of a given electrode of the first set of electrodes and the two different modulated frequency signals of a given electrode of the second set of electrodes.

4. The system according to claim 1, wherein the sound processor is configured to generate: the at least two modulated signals for each of the first set of electrodes as low frequency signals, and the at least two modulated signals for each of the second set of electrodes as high frequency signals, wherein the high frequency signals are at a higher frequency relative to the low frequency signals.

5. The system according to claim 4, wherein the sound processor is configured to select fundamental frequencies for the modulation signals, wherein selecting includes one or more of:
    a fitting assessment of specific electrode and stimulation rate combinations for a fundamental frequency range, the assessment performed by: (i) varying the specific electrode and stimulation rate combinations, and (ii) identifying, by the patient, a desired combination of electrodes and stimulation rates of the perceived harmonicity for each fundamental frequency; and
    executing a running coding strategy that selects the fundamental frequencies by performing an extraction process on the sound signal using periodicity analysis.

6. The system according to claim 5, wherein the running coding strategy selects the fundamental frequencies based on extracting: (i) a number of fundamental frequencies in the sound signal, (ii) a frequency value of each of the fundamental frequencies, and (iii) a frequency range of the electrodes.

7. The system accordingly to claim 4, wherein the first set of electrodes is located in a more apical region of the cochlea relative to the second set of electrodes, which is located in a more basal region of the cochlea.

8. A method of processing polyphonic pitch by a cochlear implant system associated with a patient, the cochlear implant system including an electrode array including a first set of electrodes for implanting on a first region of the cochlea of the patient, and a second set of electrodes for implanting on a second region of the cochlea of the patient, the method comprising:
    capturing a sound signal having polyphonic pitch; and
    for each electrode of the first set and the second set:
        generating at least two different modulated frequency signals from the sound signal, each modulated frequency signal corresponding to a different pitch in the sound signal; and
        stimulating the electrode by simultaneously applying the at least two different modulated frequency signals to the electrode,
    wherein the at least two different modulated frequency signals are applied to the electrode in an interleaved arrangement.

9. The method according to claim 8, wherein each electrode of the first set of electrodes and the second set of electrodes is configured for implantation on the cochlea at least at a minimum spatial distance from each other electrode of the first set and the second set.

10. The method according to claim 8, wherein the modulated frequency signals are generated such that a same ratio exists between the two different modulated frequency signals of a given electrode of the first set of electrodes and the two different modulated frequency signals of a given electrode of the second set of electrodes.

11. The method according to claim 8, wherein the at least two modulated frequency signals for each of the first set of electrodes are generated as low frequency signals, and the at least two modulated signals for each of the second set of electrodes are generated as high frequency signals, wherein the high frequency signals are at a higher frequency relative to the low frequency signals.

12. The method according to claim 11, further comprising selecting the fundamental frequencies for the modulation signals by one or more of:
fitting frequency relations of the patient by assessing specific electrode and stimulation rate combinations for a fundamental frequency range, the assessment being performed by: (i) varying the specific electrode and stimulation rate combinations, and (ii) identifying, by the patient, a combination perceived harmonic for each fundamental frequency; and
executing a running coding strategy that selects the fundamental frequencies by performing an extraction process on the sound signal using periodicity analysis.

13. The method according to claim 12, further comprising defining, by the running coding strategy, the fundamental frequencies based on extracting: (i) a number of fundamental frequencies in the sound signal, (ii) a frequency value of each of the fundamental frequencies, and (iii) a frequency range of the electrodes.

14. The method accordingly to claim 11, wherein the first set of electrodes is located in a more apical region of the cochlea relative to the second set of electrodes, which is located in a more basal region of the cochlea.

15. A non-transitory tangible computer program product in a computer-readable medium for processing polyphonic pitch by stimulating electrodes of an electrode array in a cochlear implant system associated with a patient, the electrode array including a first set of electrodes for implanting on a first region of the cochlea, and a second set of electrodes for implanting on a second region of the cochlea, the product comprising:
program code for capturing a sound signal having polyphonic pitch; and
for each electrode of the first set and the second set:
program code for generating at least two different modulated frequency signals from the sound signal, each modulated frequency signal corresponding to a different pitch in the sound signal; and
program code for stimulating the electrode by simultaneously applying the at least two different modulated frequencies to the electrode, wherein the at least two different modulated frequency signals are applied to the electrode in an interleaved arrangement.

16. The product according to claim 15, wherein each electrode of the first set of electrodes and the second set of electrodes is configured for implantation on the cochlea at least at a minimum spatial distance from each other electrode of the first set and the second set.

17. The product according to claim 15, wherein the modulated frequency signals are generated such that a same ratio exists between the two different modulated frequency signals of a given electrode of the first set of electrodes and the two different modulated frequency signals of a given electrode of the second set of electrodes.

18. The product according to claim 15, wherein the at least two modulated signals for each of the first set of electrodes are generated as low frequency signals, and the at least two modulated signals for each of the second set of electrodes are generated as high frequency signals, wherein the high frequency signals are at a higher frequency relative to the low frequency signals.

19. The product according to claim 18, further comprising program code for selecting fundamental frequencies for the modulation signals, wherein selecting includes one or more of:
a fitting assessment of specific electrode and stimulation rate combinations for a fundamental frequency range, the assessment being performed by: (i) varying the specific electrode and stimulation rate combinations, and (ii) identifying, by the patient, a combination perceived harmonic for each fundamental frequency; and
executing a running coding strategy that selects the fundamental frequencies by performing an extraction process on the sound signal using periodicity analysis.

20. The product according to claim 19, the further comprising program code for selecting, by the running coding strategy, the fundamental frequencies based on extracting: (i) a number of fundamental frequencies in the sound signal, (ii) a frequency value of each of the fundamental frequencies, and (iii) a frequency range of the electrodes.

21. The product accordingly to claim 18, wherein the first set of electrodes is located in a more apical region of the cochlea relative to the second set of electrodes, which is located in a more basal region of the cochlea.

22. A cochlear implant system for processing polyphonic pitch, the system comprising:
an electrode array for implanting in a cochlea of a patient, the electrode array including:
a first set of electrodes, each electrode of the first set for implanting on a first region of the cochlea, and
a second set of electrodes, each electrode of the second set for implanting on a second region of the cochlea; and
a sound processor configured to:
capture a sound signal having polyphonic pitch; and
for each electrode of the first set and the second set:
generate at least two different modulated frequency signals from the sound signal, each modulated frequency signal corresponding to a different pitch in the sound signal, and
stimulate the electrode by simultaneously applying the at least two different modulated frequency signals to the electrode,
wherein the sound processor is configured to generate the modulated frequency signals such that a same ratio exists between the two different modulated frequency signals of a given electrode of the first set of electrodes and the two different modulated frequency signals of a given electrode of the second set of electrodes.

23. A method of processing polyphonic pitch by a cochlear implant system associated with a patient, the cochlear implant system including an electrode array including a first set of electrodes for implanting on a first region of the cochlea of the patient, and a second set of electrodes for implanting on a second region of the cochlea of the patient, the method comprising:
capturing a sound signal having polyphonic pitch; and
for each electrode of the first set and the second set:
generating at least two different modulated frequency signals from the sound signal, each modulated frequency signal corresponding to a different pitch in the sound signal; and
stimulating the electrode by simultaneously applying the at least two different modulated frequency signals to the electrode,
wherein the modulated frequency signals are generated such that a same ratio exists between the two different modulated frequency signals of a given electrode of the first set of electrodes and the two different modulated frequency signals of a given electrode of the second set of electrodes.

24. A non-transitory tangible computer program product in a computer-readable medium for processing polyphonic pitch by stimulating electrodes of an electrode array in a cochlear implant system associated with a patient, the electrode array including a first set of electrodes for implanting on a first region of the cochlea, and a second set of electrodes for implanting on a second region of the cochlea, the product comprising:

program code for capturing a sound signal having polyphonic pitch; and for each electrode of the first set and the second set:

program code for generating at least two different modulated frequency signals from the sound signal, each modulated frequency signal corresponding to a different pitch in the sound signal; and program code for stimulating the electrode by simultaneously applying the at least two different modulated frequencies to the electrode, wherein the modulated frequency signals are generated such that a same ratio exists between the two different modulated frequency signals of a given electrode of the first set of electrodes and the two different modulated frequency signals of a given electrode of the second set of electrodes.

\* \* \* \* \*